United States Patent
Delonzor et al.

(10) Patent No.: US 7,373,189 B2
(45) Date of Patent: May 13, 2008

(54) SHUNT BARRIER IN PULSE OXIMETER SENSOR

(75) Inventors: Russ Delonzor, Union City, CA (US); Paul D. Mannheimer, Danville, CA (US); Michael E. Fein, Mountain View, CA (US); Don Hannula, San Luis Obispo, CA (US)

(73) Assignee: Nellcor Puritan Bennett Inc., Pleasanton, CA (US)

( * ) Notice: Subject to any disclaimer, the term of this patent is extended or adjusted under 35 U.S.C. 154(b) by 0 days.

(21) Appl. No.: 11/526,415

(22) Filed: Sep. 25, 2006

(65) Prior Publication Data

US 2007/0021660 A1     Jan. 25, 2007

Related U.S. Application Data

(60) Continuation of application No. 10/870,288, filed on Jun. 16, 2004, now Pat. No. 7,190,984, which is a continuation of application No. 10/194,156, filed on Jul. 12, 2002, now Pat. No. 6,763,255, which is a division of application No. 09/750,670, filed on Dec. 28, 2000, now Pat. No. 6,430,423, which is a division of application No. 09/085,698, filed on May 27, 1998, now Pat. No. 6,173,196, which is a continuation of application No. 08/611,151, filed on Mar. 5, 1996, now Pat. No. 5,797,841.

(51) Int. Cl.
*A61B 5/1455* (2006.01)

(52) U.S. Cl. .................. 600/310; 600/323; 600/344

(58) Field of Classification Search ........... 600/309, 600/310, 322, 323, 344

See application file for complete search history.

(56) References Cited

U.S. PATENT DOCUMENTS

| | | | |
|---|---|---|---|
| 3,769,974 A | 11/1973 | Smart et al. |
| 4,510,938 A | 4/1985 | Jobsis et al. |
| 4,830,014 A | 5/1989 | Goodman |
| 4,964,408 A | 10/1990 | Hink et al. |
| 5,035,243 A | 7/1991 | Muz |
| 5,090,410 A | 2/1992 | Saper et al. |
| 5,099,842 A | 3/1992 | Mannheimer et al. |
| 5,203,327 A | 4/1993 | Schoendorfer et al. |
| 5,209,230 A | 5/1993 | Swedlow et al. |
| 5,217,013 A | 6/1993 | Lewis et al. |
| 5,246,003 A | 9/1993 | DeLonzor |
| 5,247,932 A | 9/1993 | Chung et al. |
| 5,277,181 A | 1/1994 | Mendelson et al. |
| 5,285,783 A | 2/1994 | Secker |
| 5,337,744 A | 8/1994 | Branigan |
| 5,368,025 A | 11/1994 | Young et al. |

(Continued)

FOREIGN PATENT DOCUMENTS

EP     0127947     12/1984

*Primary Examiner*—Eric Winakur
*Assistant Examiner*—Etsub D Berhanu

(57) ABSTRACT

A pulse oximeter sensor comprising an emitter and a detector disposed on a substrate layer with a thinned portion between the emitter and the detector. A partially transparent covering layer covers the substrate layer and comprises a corresponding thinned portion. The thinned portions attenuate light shunted via the substrate layer and the partially transparent covering layer from the emitter to the detector, and may be configured such that less than 10% of the light detectable by the detector is shunted light.

34 Claims, 6 Drawing Sheets

U.S. PATENT DOCUMENTS

| | | |
|---|---|---|
| 5,402,777 A | 4/1995 | Warring et al. |
| 5,425,360 A | 6/1995 | Nelson |
| 5,452,717 A | 9/1995 | Branigan |
| 5,485,838 A | 1/1996 | Ukawa et al. |
| 5,520,177 A | 5/1996 | Ogawa et al. |
| 5,564,417 A | 10/1996 | Chance et al. |
| 5,782,757 A | 7/1998 | Diab et al. |
| 5,797,841 A | 8/1998 | Delonzor et al. |
| 6,173,196 B1 | 1/2001 | Delonzor et al. |
| 6,430,423 B2 | 8/2002 | DeLonzor et al. |
| 6,763,255 B2 | 7/2004 | DeLonzor et al. |

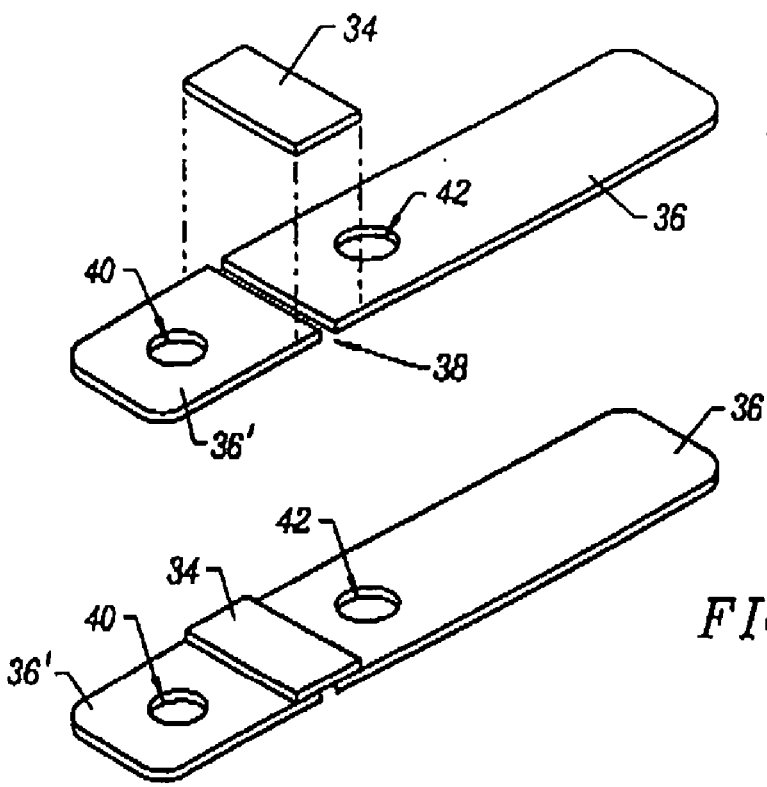
FIG. 3A
FIG. 3B
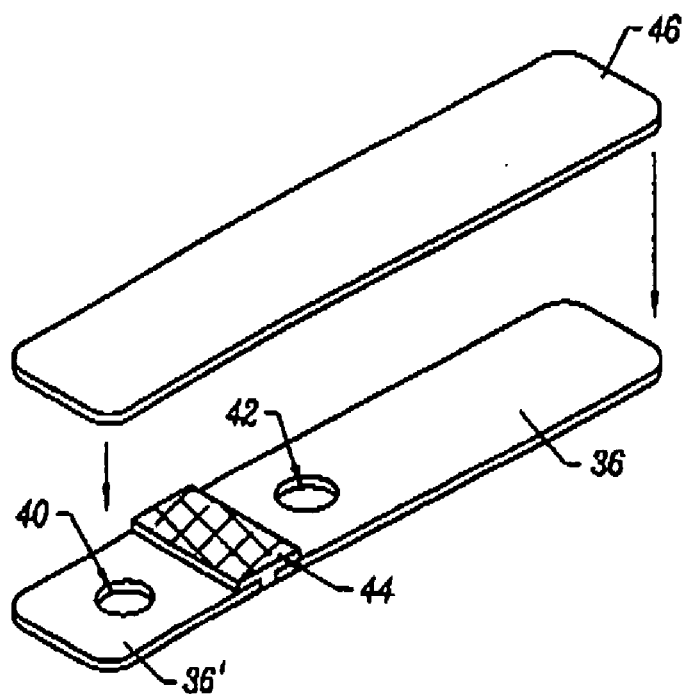
FIG. 4

SHUNT BARRIER IN PULSE OXIMETER SENSOR

CROSS-REFERENCE TO RELATED APPLICATIONS

This application is a continuation of U.S. application Ser. No. 10/870,288, filed Jun. 16, 2004, now U.S. Pat. No. 7,190,984 which is a continuation of U.S. application Ser. No. 10/194,156, filed Jul. 12, 2002, now U.S. Pat. No. 6,763,255, which is a divisional of U.S. application Ser. No. 09/750,670, filed Dec. 28, 2000, now U.S. Pat. No. 6,430,423, which is a divisional of U.S. application Ser. No. 09/085,698, filed May 27, 1998, now U.S. Pat. No. 6,173,196, which is a continuation of U.S. application Ser. No. 08/611,151, filed Mar. 5, 1996, now U.S. Pat. No. 5,797,841, the disclosures of which are incorporated by reference herein.

BACKGROUND OF THE INVENTION

The present invention relates to pulse oximeter sensors, and in particular to methods and apparatus for preventing the shunting of light between the emitter and detector without passing through blood-perfused tissue.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

One problem with such sensors is the detection of ambient light by the photodetector, which can distort the signal. Another problem is the shunting of light directly from the photo-emitter to the photodetector without passing through blood-perfused tissue. FIG. 1 illustrates two different types of light shunting that can interfere with proper detection of oxygen saturation levels. As shown in FIG. 1, a sensor 10 is wrapped around the tip of a finger 12. The sensor includes a light emitter 14 and a light detector 16. Preferably, light from emitter 14 passes through finger 12 to be detected at detector 16, except for amounts absorbed by the blood-perfused tissue.

A first type of shunting, referred to as type 1 shunting, is shunting inside the sensor body as illustrated by light path 18, shown as a wavy line in FIG. 1. Light shunts through the sensor body with the sensor body acting like a light guide or light pipe, directing light from the emitter to the detector.

A second type of shunting, referred to as type 2 shunting, is illustrated by line 20 in FIG. 1. This type of light exits the sensor itself, but reaches the detector without passing through the finger. In the embodiment shown, the light can go around the side of the finger, perhaps by being piped by the sensor body to the edges of the sensor and then jumping through the air gap between the two edges which are wrapped around the side of the finger.

The problem of light shunting can be exacerbated by layers placed over the emitter and detector. Often, it is desirable not to have the emitter and detector in direct contact with the patient's skin because motion artifacts can be reduced by placing a thin layer of adhesive between these components and the skin. Thus, the emitter and detector are typically covered with a clear layer which isolates them from the patient, but allows light to transmit through. The feature of allowing light to transmit through the layer also provides the capability for the clear layer to provide a wave guide effect to shunt light around the finger to the detector.

Such layers covering the emitter and detector can be originally included in the sensor, or can be added during a reinforcing or modifying procedure, or during a remanufacture of the sensor. In a remanufacture of a sensor, a sensor which has been used may have its outer, adhesive transparent layer removed. Such a layer is shown in FIG. 2 as a transparent layer 22 over a sensor 10. Layer 22 is an adhesive, transparent layer placed over a substrate layer 24, upon which emitter 14 and detector 16 are mounted, along with any other associated electronics. Layer 22 thus serves both to protect the emitter and detector from the patient, and to adhere the sensor to the patient. During remanufacture, this layer can be stripped off, and a new layer placed thereon.

Alternately, layer 22 may be left in place. Such a sensor, with an adhesive outer layer, may be a disposable sensor, since it would not be desirable to have the same adhesive used from one patient to another, and an adhesive is difficult to clean without removing the adhesive. Accordingly, a modification of such a sensor may involve laminating sensor 10 to cover over the adhesive, by adding an additional lamination layer 23 (shown partially broken away) over layer 22. The lamination layer is itself another layer for shunting light undesirably from the emitter to the detector. Once laminated, in one method, the sensor is then placed into a pocket 26 of a sheath 32. Sheath 32 includes a transparent cover 28 on an adhesive layer 30. Layer 30 is adhesive for attaching to a patient. Layer 28 may also optionally be adhesive-coated on the side which faces the patient. Such a modified sensor can be reused by using a new sheath 32. Transparent layer 28 forms yet another shunting path for the light.

A commercially available remanufactured sensor, similar in design to the sensor of FIG. 2, is available from Medical Taping Systems, Inc. Another example of a sheath or sleeve for a sensor is shown in U.S. Pat. No. 4,090,410, assigned to Datascope Investment Corp.

In addition, when a sheath such as 32 is folded over the end of a patient's finger, it has a tendency to form wrinkles, with small air gaps in-between the wrinkled portions. The air gaps can actually exacerbate the shunting problem, with light jumping more easily through the air gaps from one portion of the transparent layer to another.

Other types of sensors have not used a solid transparent layer 22 as shown in FIG. 2. For instance, the Nellcor Puritan Bennett R-15 Oxisensor® and N-25 Neonatal/Adult Oxisensor products use a white-colored substrate with separate transparent strips placed over the emitter and detector (such as strips 11 and 13 illustrated in FIG. 1). The transparent strips are adhesive for adhering to the patient. Since two strips are used, an air gap (gap 15 in FIG. 1) occurs between the transparent layers. As noted above, light can jump such an air gap, and thus a gap by itself may not eliminate all shunting problems. The use of a dark-colored substrate may reduce the amount of shunting, if the selected color is opaque to the wavelengths of interest from the emitter, 650 nm red and 905 nm infrared in a typical implementation. However, the white substrate typically used in the R-15 and N-25 sensors is substantially translucent and thus has limited light blocking qualities.

It has been found that shunted light can significantly affect the accuracy of oxygen saturation readings using a pulse oximeter. Accordingly, there is a need to develop a barrier to such light to improve the accuracy of pulse oximeter sensors.

BRIEF SUMMARY OF THE INVENTION

The present invention provides a sensor having an emitter(s) and a detector, with a layer having a first portion over the emitter and a second portion over the detector. A shunt barrier is included between the first and second portions of the overlying layer to substantially block transmission of radiation of the wavelengths emitted by the emitter(s). Preferably, the shunt barrier reduces the radiation shunted to less than 10% of the total radiation detected, and more preferably to less than 1% of the total radiation detected, when the sensor is used on patients having the most opaque tissue of all patients in the target population.

In particular for a remanufactured or reinforced or modified sensor, the barrier is added in at least one, and more preferably in all, of the extra layers added or replaced during the remanufacturing, reinforcing or modifying process. The barrier of the present invention may take a number of specific forms. In one embodiment, a woven or fiber material is included between the emitter and detector. In another embodiment, the layer in-between the emitter and detector is pigmented with a color which is substantially opaque for the wavelengths of interest, while the portion above the emitter and detector is substantially transparent. In another embodiment, the entire layer is partially opaque, but is thin enough so that light transmitted through is able to penetrate the partially opaque layer, while light traveling the length of the layer would have a greater distance to travel and would be substantially absorbed.

Another shunt barrier is the insertion of perforations in the layer between the emitter and detector. The perforations may provide air gaps, which still will shunt some light, or may be filled with other material or have the insides of the perforations colored with an opaque color.

In another embodiment, the layer between the emitter and detector is made very thin, such as by embossing, welding or heat sealing. The thinness of the material will limit its effectiveness as a light pipe in the wavelengths of interest, red and infrared.

In another embodiment, a deformable, opaque material, such as foam, is included between the emitter and detector, to be compressed upon application to a finger or other body part and fill any gap that might otherwise form through wrinkles or otherwise upon application of the sensor.

In another embodiment, an adhesive is applied in a gap between two layers over the emitter and detector, to cause an underlying layer to come in contact with the patient, thus filling the air gap and preventing shunting along that path.

While most of the illustrative examples given in this specification are shown as sensors adapted to be wrapped onto a digit, so that light is transmitted through the digit, it will be clear to those skilled in the art that the design principles illustrated may be applied to any "transmittance" or "reflectance" sensors for pulse oximetry. A typical reflectance sensor is the Nellcor Puritan Bennett RS-10.

For a further understanding of the nature and advantages of the invention, reference should be made to the following description taken in conjunction with the accompanying drawings.

BRIEF DESCRIPTION OF THE DRAWINGS

FIGS. 3A and 3B are diagrams of one embodiment of a shunt barrier showing an opaque film abutting both an air gap and another layer;

FIG. 4 is a diagram of a sensor with a woven or fiber material for a shunt barrier;

DETAILED DESCRIPTION OF THE INVENTION

Figure 1:
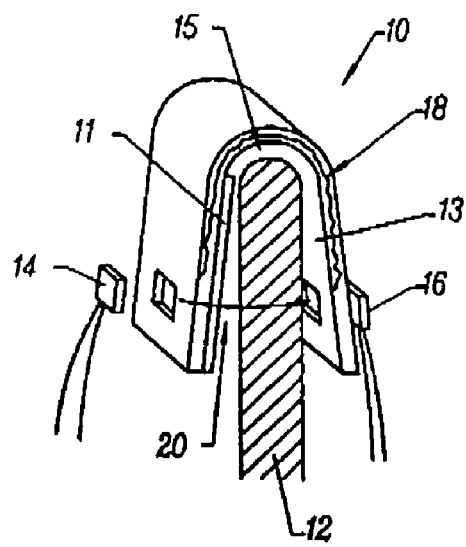
FIG. 1 is a diagram illustrating the shunting that occurs upon the placement of a sensor over a finger.

FIGS. 3A and 3B illustrate the use of an opaque film adjacent another layer or an air gap to absorb shunting light. FIG. 3A shows the opaque film 34, before assembly being placed over layers 36, 36' separated by an air gap 38. Layers 36, 36' may be mounted on a common substrate (not shown). Holes 40 and 42 are shown for the emitter and detector. Alternately, these can be windows or simply a solid portion of a transparent layer. FIG. 3B shows the assembled lower layer and opaque film layer 34. As light attempts to shunt from emitter area 40 to detector area 42, either passing through the air gap 38 or through layers 36 and 36', it will bounce back and forth between the boundaries of the layer and through the air gap. Some of the light that would normally hit the top end of layer 36 or 36' and bounce back into the middle of the layer, will instead pass into and be absorbed by opaque layer 34, which is tightly coupled to the layers 36 and 36'.

FIG. 4 illustrates the use of a woven or fiber material 44 on layers 36 and 36', and filling the air gap 38 of FIG. 3A. Fibers in the material will absorb light, thus attenuating light attempting to shunt from emitter area 40 to detector area 42. An additional cover layer 46 may be placed over the assembly, and which will need to be at least partially transparent for light to escape and be detected. Layer 46 can function as another shunting layer. By abutting up against the woven or fiber material 44, light will be absorbed out of that layer in the same manner as the opaque film 34 of FIG. 3A and B. Alternately, the fiber and woven material can be inserted into layer 46 between the emitter and detector.

Figure 5:
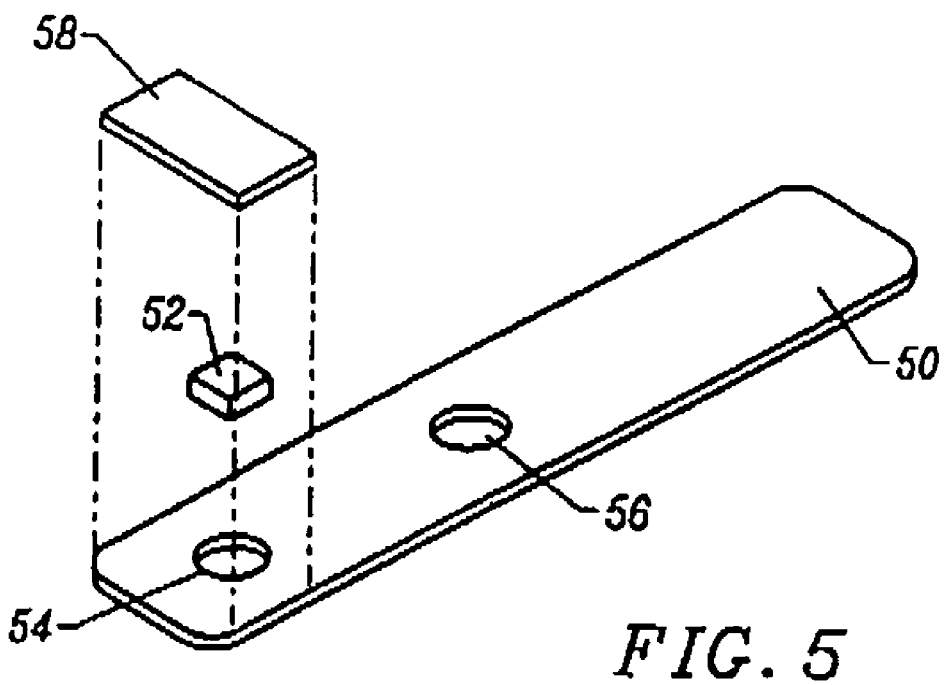
FIG. 5 is a diagram of a sensor with a partially opaque material for a shunt barrier, with a trade-off between transmission intensity and preventing shunting.

FIG. 5 shows an alternate embodiment in which a layer 50 is used with an emitter 52 placed on top of it. Alternately, layer 50 could have holes 54 and 56 over the emitter and detector, with the emitter 52 being placed through hole 54 onto an underlying layer. A partially opaque layer 58 is placed above emitter 52 in the embodiment shown. Layer 58 may extend a portion of the way or all of the way over to where the detector is. The opacity of layer 58 is chosen in conjunction with its thickness to allow transmission of substantially all of the light from emitter 52 through the layer, while substantially reducing the amount of light shunted in a path transverse through the layer from the emitter to the detector. Layer 58 preferably attenuates the shunted light so that it is less than 10%, and more preferably less than 1% of the total light received by the detector. Additionally, of the light detected by the detector and converted into electrical signal, the portion of the electrical signal due to shunted light is preferably less than 10% and more preferably less than 1% of the signal value.

The layer may be made substantially opaque through coloring. One such color would be a gray created by suspension of carbon black particles in the base material of the layer. This would be substantially opaque to both red and infrared.

Figure 6:
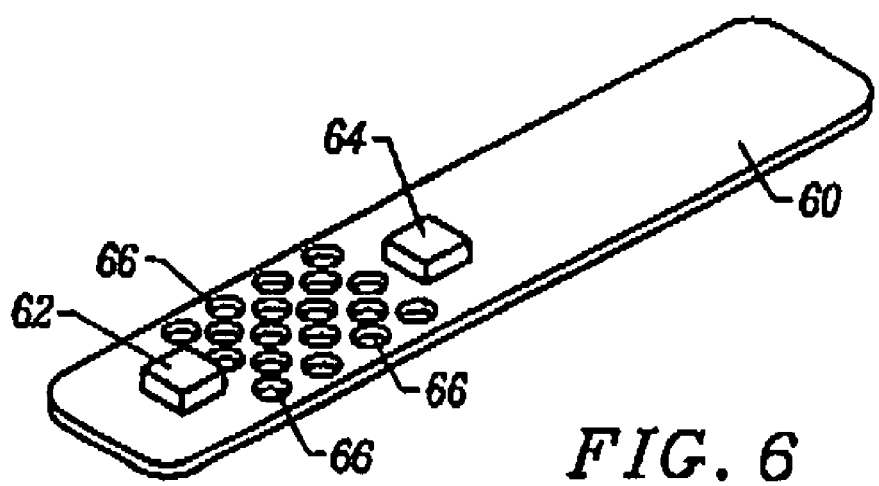
FIG. 6 is a diagram of a sensor using perforations as a shunt barrier.

FIG. 6 shows another embodiment of the invention in which a layer 60 over an emitter 62 and detector 64 has a series of perforations 66. These perforations block the light path and scatter the light attempting to shunt between the emitter 62 and detector 64 through layer 60. Although light tends to jump air gaps, by providing multiple air gaps in different orientations, the light can be somewhat effectively scattered. Alternately, the perforations could be filled with a colored filling material or putty to block the light that might otherwise jump the air gaps, or could have the inside walls of the perforations colored. Alternately, embossing (or other variations in thickness) could be used rather than perforations.

Figure 7:
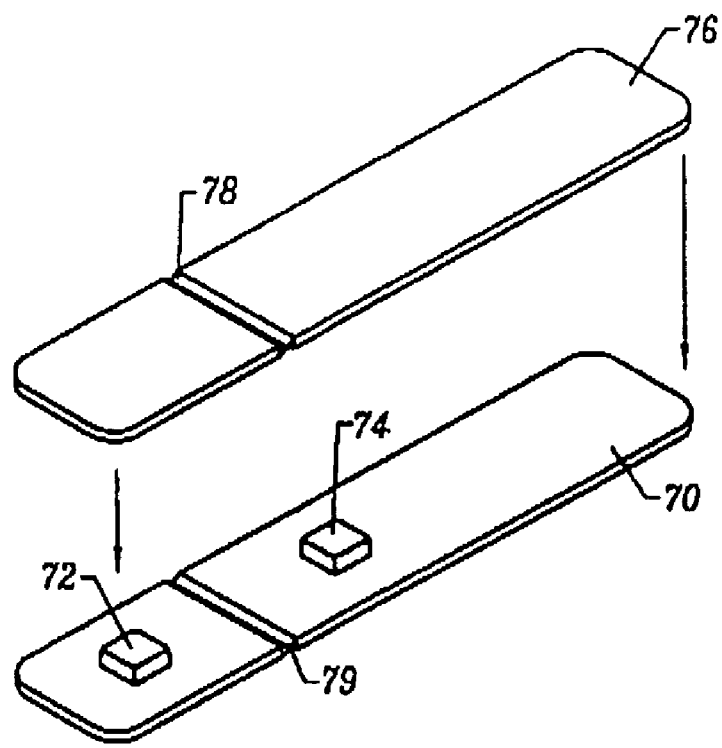
FIG. 7 is a diagram of a sensor with a thinned layer between emitter and detector as a shunt barrier.

FIG. 7 illustrates a layer 70 having an emitter 72 and detector 74, covered by another layer 76. Layer 76 may be partially transparent for light to exit from emitter 72 and re-enter to detector 74. Layer 76 has a thinned portion 78, and layer 70 has a corresponding thinned portion 79. These portions make the layers thin in that area, thus limiting the amount of light that may be shunted. The layer could be made thin by a number of techniques, such as embossing, welding or heat sealing. The width of the thinned area could be varied, and the shape could be varied as desired. For instance, the thinned area could extend around the sides of the emitter and detector, to prevent shunting of light from the edges of the layers when they are wrapped around a finger.

The thinness of the layer contributes to absorption of the light because light which is traveling in a thin layer will more often bounce off the layer boundaries than it would in a thick layer. This provides more chances to escape the layer and be lost or absorbed in an adjoining layer with absorption characteristics.

The thickness is preferably less than 0.25 mm and more preferably no more than 0.025 mm. The length of the thin section is preferably greater than 1 mm and more preferably greater than 3 mm.

The thin layer approach could be applied to a re-manufacture or other modification of a sensor which involves adding a layer over the emitter and detector. The entire layer could be made thin, preferably less than 0.25 mm, more preferably no more than 0.025 mm, in order to limit its shunting effect.

Figure 8:
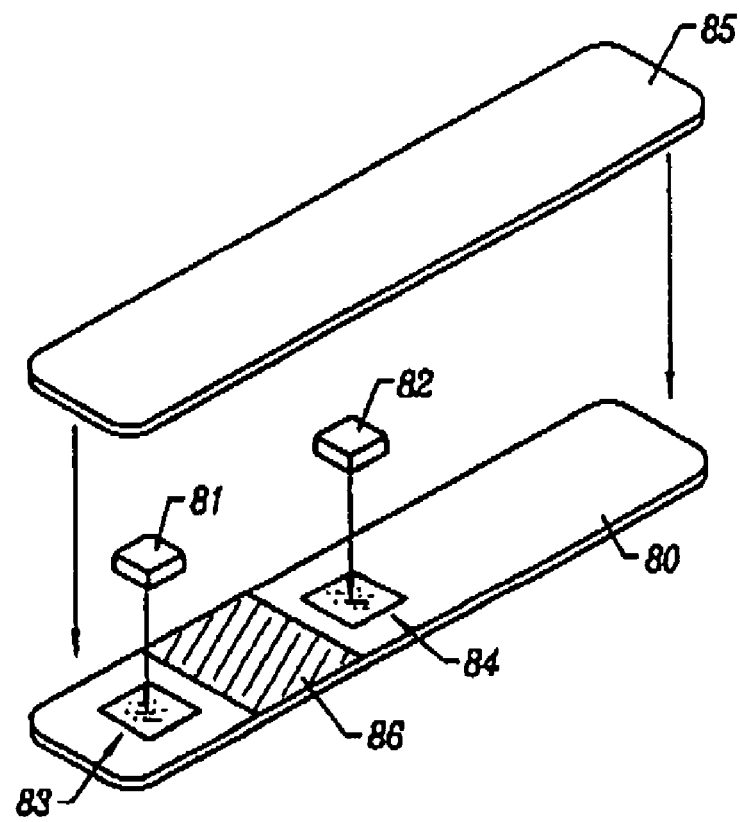
FIG. 8 is a diagram of a sensor using differential coloring as a shunt barrier.

FIG. 8 shows a sensor having a layer 80 for an emitter 81 and a detector 82, having transparent windows 83 and 84, respectively. A substrate layer 85 supports the emitter and detector, with light being transmitted through transparent window 83 and received through window 84. In one embodiment, the entire layer 80 is opaque, leaving transparent portions 83 and 84. Alternately, the entire layer 80 may be transparent, or of one color with the windows of another or transparent. In addition, a portion 86 of layer 80 between the emitter and detector may be colored a substantially opaque color to prevent the shunting of light of the wavelengths of interest. In alternate embodiments, portion 86 may be of different shapes, and may partially or totally enclose the windows for the emitter and detector.

Figure 9:
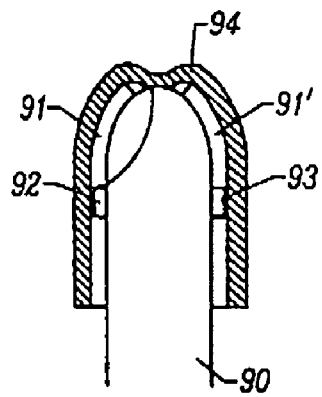
FIG. 9 is a diagram of a sensor using an adhesive in a gap between layers over the emitter and detector for a shunt barrier.

FIG. 9 shows another embodiment of a sensor according to the present invention mounted on a finger 90. Two portions of a first layer, 91, 91' have the emitter 92 and detector 93, respectively, attached to them. A break between layers 91 and 91' is provided in between the emitter and detector, which will be at the tip of finger 90. Normally, this gap would provide an air gap through which light can be shunted between the emitter and detector across the top of the finger. However, by using a backing layer 94, with an adhesive in the portion between layers 91 and 91', this layer can stick to the tip of finger 90, removing the air gap and thus substantially preventing shunting between the layers.

Figure 10:
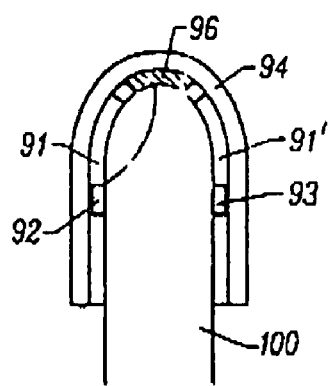
FIG. 10 is a diagram of a sensor using a foam pad between the emitter and detector as a shunt barrier.

An alternate embodiment is shown in FIG. 10, with the finger 100 having a sensor with layers 91 and 91' and emitter 92 and detector 93 as in FIG. 9. Here, however, a separate layer 94 is provided with a foam or other resilient or compressible pad 96 mounted on layer 94 between layers 91 and 91'. This material will compress against the tip of the finger, thus also blocking the air gap and preventing the shunting of light if the material is made of a substantially opaque material, such as a color that is substantially opaque to the wavelengths of interest (e.g., red and infrared), or is made of woven material or other material opaque to the light.

Figure 11:
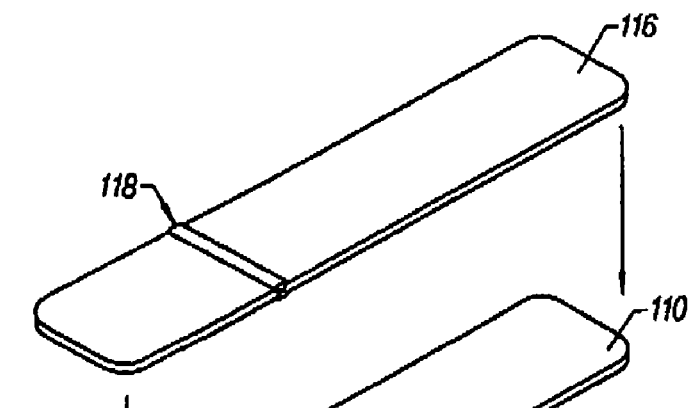
FIG. 11 is a diagram of a sensor using a solid barrier as a shunt barrier.

FIG. 11 is another embodiment of the present invention showing a layer 110 having an emitter 112 and a detector 114 mounted thereon. A covering, transparent layer 116 provides a covering and a window for the transmission and detection of light. Shunting of light is prevented by crimping the layers with a metal or other crimp 118, 120. The metal or other material is substantially opaque to the shunted light of the wavelengths of interest, and completely penetrates the layer, or substantially penetrates the layer.

Figure 12:
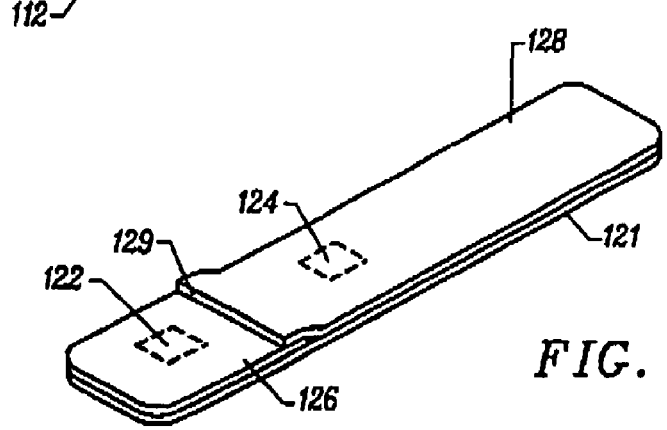
FIG. 12 is a diagram of a sensor showing the use of overlapping layers as a shunt barrier.

FIG. 12 shows an alternate embodiment in which a layer 121 has an emitter 122 and a detector 124 (both shown in phantom) mounted thereon. Over the emitter area is a first transparent layer 126, with a second transparent layer 128 over the detector 124. As can be seen, the two layers are overlapping, with the end 129 of layer 128 being on top of layer 126. Thus, instead of an air gap, any shunted light from layer 128 is deflected to be above layer 126, and vice versa. Alternately, since the light will originate from the emitter, it may be more preferable to have the layer overlaying the emitter be on top of the layer overlaying the detector. In the overlapping portion, a radiation blocking layer may be included, such as a colored adhesive.

Figure 13:
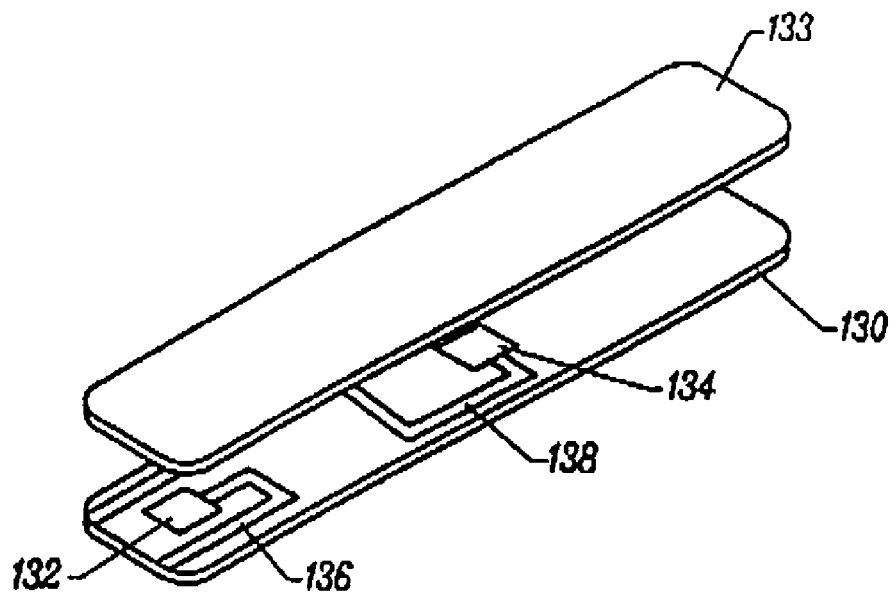
FIG. 13 is a diagram of a sensor using a barrier of metal traces forming a tortuous path between emitter and detector as a shunt barrier.

FIG. 13 shows an alternate embodiment of the present invention in which a flexible circuit is printed onto a layer 130. As shown, emitter 132 and detector 134 are mounted on the flexible layer 130. A covering layer 133 is provided. Layers 130 and 133 may be partially or substantially opaque to prevent the shunting of light. In between the layers, metal traces 136 and 138 can be used to block the shunting of light. Instead of making these traces run lengthwise, leaving a clear path between the emitter and detector, they instead follow a tortuous path. This tortuous path not only goes lengthwise, but also goes across the width of the layer 130, thus providing a barrier to block shunting the light between the emitter and detector.

Figure 2:
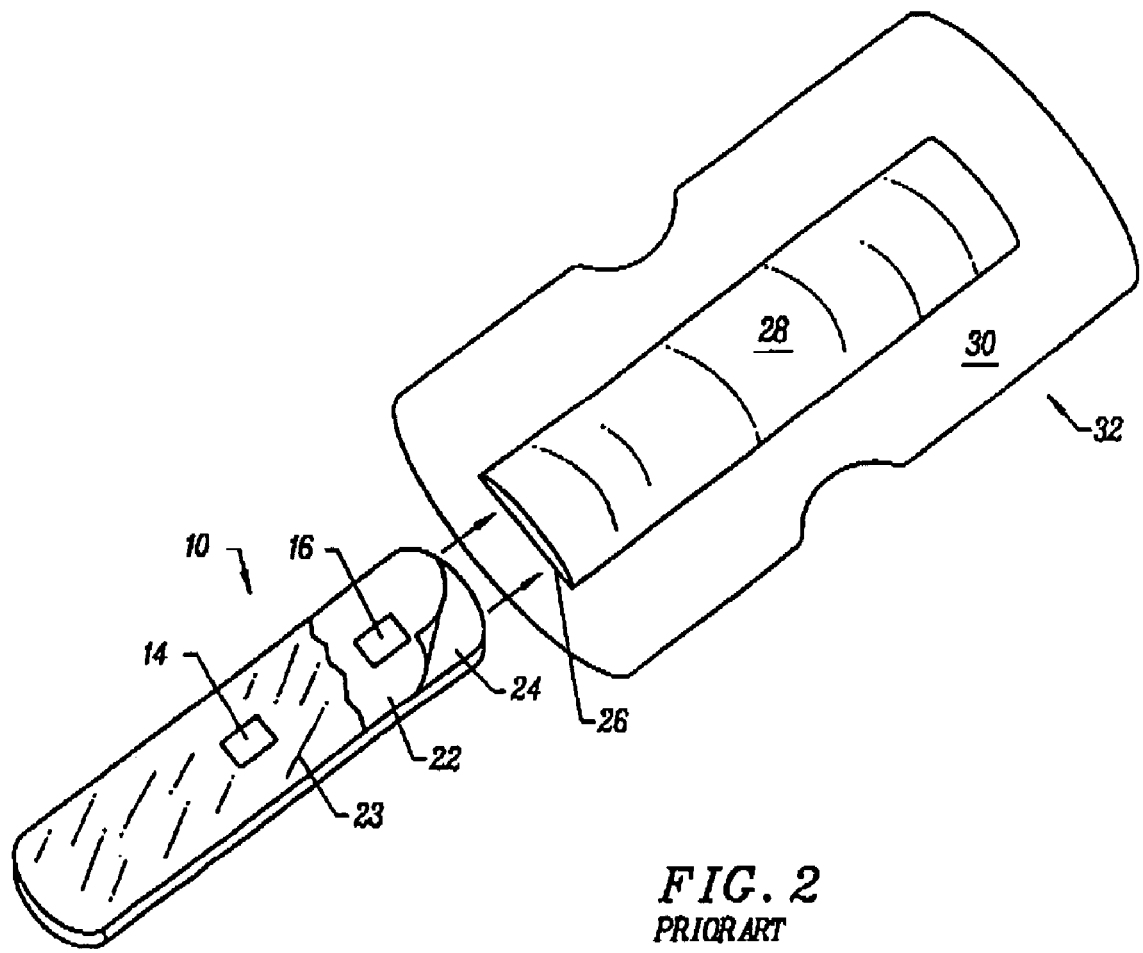
FIG. 2 is a diagram of a sensor being placed within a reusable sheath in a sensor modification operation.
Figure 14:
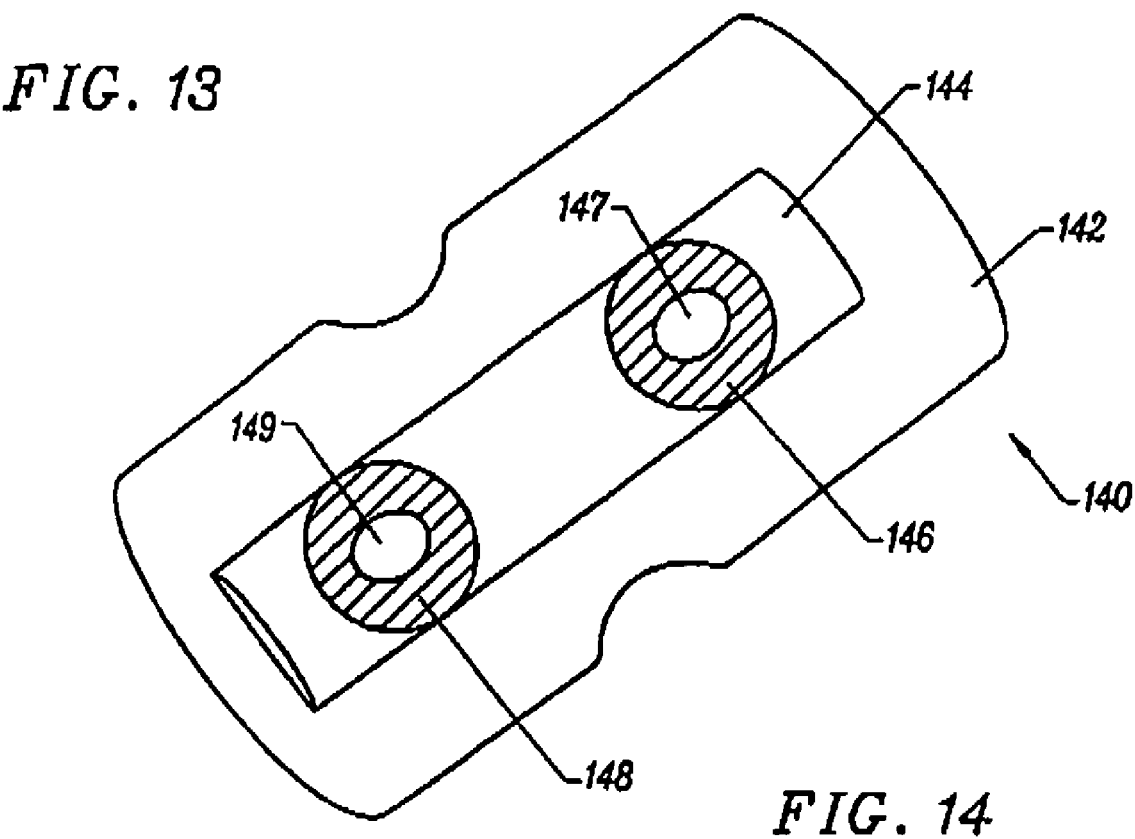
FIG. 14 is a diagram of a sheath incorporating a colored ring around the emitter and detector windows as a shunt barrier.

FIG. 14 shows another embodiment of the present invention for modifying a sheath such as sheath 32 of FIG. 2. FIG. 14 shows a sheath 140 having a first, adhesive layer 142, and a second layer 144 being transparent and forming a pocket for the insertion of a sensor. Layer 144 has opaque colored rings 146 and 148 surrounding windows 147 and 149, respectively. These windows allow the transmission of light to and from the emitter and detector, while the opaque rings prevent the shunting of light through transparent layer 144. Alternately, more or less of the transparent layer 144 could be colored with an opaque color to prevent the shunting of light.

Alternately, in the embodiment of FIG. 14, windows 147 and 149 could be one color, while areas 146 and 148, which may extend over the rest of the layer 144, could be of a second color. The second color would be chosen to prevent shunting, while the first color would be chosen to allow the transmission of light while also being of a color which is compatible with the calibration data for an oximeter sensor. If the color over the emitter and detector is not chosen properly, it may interfere with the choice of a proper calibration curve in the oximeter sensor for the particular wavelength of the emitter being used. Typically, LEDs of slightly varying wavelengths are used, with a coding resistor indicating the exact wavelength. The coding resistor is used to choose a particular calibration curve of coefficients in the oximeter sensor. Thus, by using a differentially-colored sheath or reinforcing laminate or other layer, with the layer near the emitter and detector chosen to be white, clear or other color which does not interfere with the calibration, shunting can be prevented while allowing the sensor to be used without affecting its standard calibration. Preferably, the regions over the emitter and detector have a radius extending at least 2 mm. beyond the borders of the emitter and detector, and preferably at least 5 mm beyond the borders of the emitter and detector.

Any of the shunt barriers described above could be incorporated into layer 144 of sheath 140 of FIG. 14. Alternately, or in addition, the shunt barriers could be incorporated into a lamination or other layer placed over a sensor in a modifying process. Such a modifying process may, for instance, place a non-adhesive layer over an adhesive layer to convert a disposable sensor into a reusable sensor. The shunt barriers described above may also be in an original layer in a sensor, or in a replacement layer added in a remanufacturing process for recycling disposable sensors.

As will be understood by those of skill in the art, the present invention may be embodied in other specific forms without departing from the spirit or essential characteristics thereof. Accordingly, the foregoing description is intended to be illustrative, but not limiting, of the scope of the invention which is set forth in the following claims.

What is claimed is:

1. A sensor comprising:
   a substrate layer;
   a light emitter coupled to the substrate layer;
   a light detector coupled to the substrate layer; and
   a layer coupled to the substrate layer over the light emitter and the light detector, wherein the layer comprises a length, a width, and a thickness, the length being generally greater than the width, and the width being generally greater than the thickness, and wherein the layer comprises a thinned portion of its thickness located between the light emitter and the light detector, the thinned portion having a reduced thickness with respect to portions of the layer disposed adjacent the light emitter and the light detector.

2. The sensor of claim 1, wherein the substrate layer comprises a length, a width, and a thickness, the length being generally greater than the width, and the width being generally greater than the thickness, and wherein the substrate layer further comprises a thinned portion of its thickness located between the emitter and the detector, the thinned portion of the substrate layer having a reduced thickness with respect to portions of the substrate layer adjacent the light emitter and the light detector.

3. The sensor of claim 2, wherein the thinned portion of the substrate layer is generally aligned with the thinned portion of the layer.

4. The sensor of claim 1, wherein the thinned portion of the layer is configured to attenuate light shunted from the light emitter to the light detector such that less than 10% of light detectable by the light detector is shunted light.

5. The sensor of claim 1, wherein the thinned portion of the layer is configured to attenuate light shunted from the light emitter to the light detector such that less than 1% of light detectable by the light detector is shunted light.

6. The sensor of claim 1, wherein the thinned portion at least partially surrounds the light detector.

7. The sensor of claim 1, wherein the thinned portion at least partially surrounds the light emitter.

8. The sensor of claim 1, wherein the thinned portion is substantially linear and extends across the layer in a direction substantially perpendicular to a line connecting the light emitter and the light detector.

9. The sensor of claim 1, wherein the thinned portion of the layer bisects the length of the layer at a location substantially equidistant from the light emitter and the light detector.

10. The sensor of claim 1, wherein the thinned portion of the layer comprises a length, the length of the thinned portion of the layer being generally aligned with the length of the layer, wherein the length of the thinned portion is more than 3 millimeters.

11. The sensor of claim 1, wherein the thinned portion of the layer comprises a length and a width, the length of the thinned portion of the layer being generally aligned with the length of the layer, and the width of the thinned portion of the layer being generally aligned with the width of the layer, wherein the width of the thinned portion of the layer is varied along the length of the thinned portion of the layer.

12. The sensor of claim 1, wherein the thinned portion of the layer has a thickness of less than 0.025 millimeters.

13. The sensor of claim 1, wherein the thinned portion of the layer comprises an embossed portion, a welded portion, or a heat sealed portion.

14. The sensor of claim 1, wherein the layer is at least partially transparent to light emitted by the light emitter.

15. The sensor of claim 1, wherein one side of the layer comprises an adhesive for adhering the sensor to a tissue location on a patient.

16. A sensor substrate comprising:
a base layer, wherein one end of the base layer comprises a location for a light emitter, and another end of the base layer comprises a location for a light detector; and
a layer coupled to the base layer over the location for the light emitter and the location for the light detector, wherein the layer comprises a length, a width, and a thickness, the length being generally greater than the width, and the width being generally greater than the thickness, and wherein the layer comprises a thinned portion of its thickness located between the location for the light emitter and the location for the light detector, the thinned portion having a reduced thickness with respect to portions of the layer disposed adjacent the location for the light emitter and the location for the light detector.

17. The sensor substrate of claim 16, wherein the base layer comprises a length, a width, and a thickness, the length being generally greater than the width, and the width being generally greater than the thickness, and wherein the base layer further comprises a thinned portion of its thickness located between the location for the light emitter and the location for the light detector, the thinned portion of the base layer having a reduced thickness with respect to portions of the base layer adjacent the location for the light emitter and the location for the light detector.

18. The sensor substrate of claim 17, wherein the thinned portion of the base layer is generally aligned with the thinned portion of the layer.

19. The sensor substrate of claim 17, wherein the thinned portion of the base layer bisects the length of the base layer at a location substantially equidistant from the light emitter and the light detector.

20. The sensor substrate of claim 17, wherein the thinned portion of the base layer comprises a length and a width, the length of the thinned portion of the base layer being generally aligned with the length of the base layer, and the width of the thinned portion of the base layer being generally aligned with the width of the base layer, wherein the width of the thinned portion of the base layer is varied along the length of the thinned portion of the base layer.

21. The sensor substrate of claim 16, wherein the thinned portion of the layer bisects the length of the layer at a location substantially equidistant from the light emitter and the light detector.

22. The sensor substrate of claim 16, wherein the thinned portion of the layer comprises a length and a width, the length of the thinned portion of the layer being generally aligned with the length of the layer, and the width of the thinned portion of the layer being generally aligned with the width of the layer, wherein the width of the thinned portion of the layer is varied along the length of the thinned portion of the layer.

23. The sensor substrate of claim 16, wherein one side of the layer comprises an adhesive for adhering the sensor to a tissue location on a patient.

24. A method of manufacturing a sensor comprising:
providing a light detector and a light emitter coupled to a substrate layer; and
providing a layer coupled to the substrate layer over the light emitter and the light detector, wherein the layer comprises a length, a width, and a thickness, the length being generally greater than the width, and the width being generally greater than the thickness, and wherein the layer comprises a thinned portion of its thickness located between the light detector and the light emitter, the thinned portion having a reduced thickness with respect to portions of the layer disposed adjacent the light emitter and the light detector.

25. The method of claim 24, wherein the substrate layer comprises a length, a width, and a thickness, the length being generally greater than the width, and the width being generally greater than the thickness, and wherein the substrate layer further comprises a thinned portion of its thickness located between the light emitter and the light detector, the thinned portion of the substrate layer having a reduced thickness with respect to portions of the substrate layer adjacent the light emitter and the light detector.

26. The method of claim 24, wherein the thinned portion of the layer is configured to attenuate light shunted from the light emitter to the light detector such that less than 10% of light detectable by the light detector is shunted light.

27. The method of claim 24, wherein the thinned portion of the layer is configured to attenuate light shunted from the light emitter to the light detector such that less than 1% of light detectable by the light detector is shunted light.

28. A sensor comprising:
a substrate layer comprising a location for a light emitter and a location for a light detector, wherein the substrate layer comprises a length, a width, and a thickness, the length being generally greater than the width, and the width being generally greater than the thickness, and wherein the substrate layer further comprises a thinned portion of its thickness located between the location for the light emitter and the location for the light detector, the thinned portion of the substrate layer having a reduced thickness with respect to portions of the substrate layer adjacent the location for the light emitter and the location for the light detector;
a light emitter coupled adjacent the location for the light emitter; and
a light detector coupled adjacent the location for the light detector.

29. The sensor of claim 28, wherein the thinned portion of the substrate layer is configured to attenuate light shunted from the light emitter to the light detector such that less than 10% of light detectable by the light detector is shunted light.

30. The sensor of claim 28, wherein the thinned portion of the substrate layer is configured to attenuate light shunted from the light emitter to the light detector such that less than 1% of light detectable by the light detector is shunted light.

31. A method of operating a sensor comprising:
emitting light at a patient with a light emitter coupled to a layer; and
detecting light from the patient with a light detector coupled to the layer, wherein the layer comprises a length, a width, and a thickness, the length being generally greater than the width, and the width being generally greater than the thickness, and wherein the layer comprises a thinned portion of its thickness located between the light detector and the light emitter, wherein the thinned portion is configured to attenuate light shunted from the light emitter to the light detector through the layer.

32. The method of claim 31, wherein the layer is coupled to a substrate layer, the substrate layer comprising a length, a width, and a thickness, the length being generally greater than the width, and the width being generally greater than the thickness, and wherein the substrate layer further comprises a thinned portion of its thickness located between the light emitter and the light detector, wherein the thinned portion is configured to attenuate light shunted from the light emitter to the light detector through the substrate layer.

33. The method of claim 31, wherein the thinned portion of the layer is configured to attenuate light shunted from the light emitter to the light detector such that less than 10% of light detectable by the light detector is shunted light.

34. The method of claim 31, wherein the thinned portion of the layer is configured to attenuate light shunted from the light emitter to the light detector such that less than 1% of light detectable by the light detector is shunted light.

* * * * *